US010646353B2

(12) United States Patent
Lechmann et al.

(10) Patent No.: US 10,646,353 B2
(45) Date of Patent: May 12, 2020

(54) INTERVERTEBRAL PROSTHESIS OR DISK PROSTHESIS

(71) Applicant: DePuy Synthes Products, Inc., Raynham, MA (US)

(72) Inventors: Beat Lechmann, Grenchen (CH); Robert Frigg, Bettlach (CH); Roger Buerki, Bettlach (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/106,727

(22) Filed: Aug. 21, 2018

(65) Prior Publication Data
US 2019/0099277 A1   Apr. 4, 2019

Related U.S. Application Data

(63) Continuation of application No. 15/623,707, filed on Jun. 15, 2017, now Pat. No. 10,085,851, which is a
(Continued)

(51) Int. Cl.
*A61F 2/44* (2006.01)
*A61F 2/30* (2006.01)
*A61F 2/46* (2006.01)

(52) U.S. Cl.
CPC .......... *A61F 2/447* (2013.01); *A61F 2/30771* (2013.01); *A61F 2/441* (2013.01);
(Continued)

(58) Field of Classification Search
CPC .................... A61F 2/4455; A61F 2/447; A61F 2002/4475; A61F 2002/448
See application file for complete search history.

(56) References Cited

U.S. PATENT DOCUMENTS 4,338,925 A    7/1982  Miller
4,405,249 A    9/1983  Scales
(Continued)

FOREIGN PATENT DOCUMENTS

DE    197 10 392 C1    7/1999
FR    2 820 630 A1     8/2002
(Continued)

OTHER PUBLICATIONS

U.S. Appl. No. 11/587,723, filed Sep. 4, 2007, Intervertebral Prosthesis or Disk Prosthesis.
(Continued)

*Primary Examiner* — Lynnsy M Summitt
(74) *Attorney, Agent, or Firm* — Nutter McClennen & Fish LLP

(57) ABSTRACT

An intervertebral prosthesis or disk prosthesis comprising a front side, a rear side, an upper side which can be placed on the base plate of vertebral body, a lower side which can be placed on the base plate of a vertebral body, a right side, a left side, a cavity which can receive a fluid hydraulic osteocementum, an opening in the cavity and several outlets out from the cavity. The total of the transversal surfaces of the outlets $S_V$ on the front side, the total of the transversal surfaces of the outlets $S_H$ on the rear side, the total of the transversal surfaces of the outlets $S_R$ on the right side and the total of the transversal surfaces of the outlets on the left side satisfy the following conditions: $S_L > S_R$ or $S_R > S_L$ or $S_H > S_V$ or $S_V > S_H$.

13 Claims, 7 Drawing Sheets

Related U.S. Application Data continuation of application No. 14/638,196, filed on Mar. 4, 2015, now Pat. No. 9,700,432, which is a continuation of application No. 11/587,723, filed as application No. PCT/CH2004/000250 on Apr. 26, 2004, now Pat. No. 8,992,618.

(52) U.S. Cl.
CPC .............. *A61F 2/442* (2013.01); *A61F 2/446* (2013.01); *A61F 2/46* (2013.01); *A61F 2002/30593* (2013.01); *A61F 2002/30777* (2013.01); *A61F 2002/30785* (2013.01); *A61F 2002/30789* (2013.01); *A61F 2002/30841* (2013.01); *A61F 2002/448* (2013.01); *A61F 2002/4631* (2013.01); *A61F 2310/00353* (2013.01)

(56) References Cited

U.S. PATENT DOCUMENTS

| | | | |
|---|---|---|---|
| 4,736,738 A | | 4/1988 | Lipovsek et al. |
| 4,863,476 A | | 9/1989 | Shepperd |
| 5,123,926 A | | 6/1992 | Pisharodi |
| 5,214,987 A | | 6/1993 | Fenton, Sr. |
| 5,397,364 A | | 3/1995 | Kozak et al. |
| 5,425,772 A | * | 6/1995 | Brantigan .............. A61F 2/447 606/247 |
| 5,571,189 A | | 11/1996 | Kuslich |
| 5,665,122 A | | 9/1997 | Kambin |
| 5,669,909 A | * | 9/1997 | Zdeblick ............ A61B 17/1671 606/247 |
| 5,697,932 A | | 12/1997 | Smith et al. |
| 5,888,224 A | | 3/1999 | Beckers et al. |
| 5,910,315 A | * | 6/1999 | Stevenson ............ A61F 2/4601 424/422 |
| 6,039,761 A | | 3/2000 | Li et al. |
| 6,048,343 A | | 4/2000 | Mathis et al. |
| 6,059,829 A | | 5/2000 | Schlaphfer |
| 6,110,179 A | | 8/2000 | Flivik et al. |
| 6,123,705 A | | 9/2000 | Michelson |
| 6,176,882 B1 | | 1/2001 | Biedermann et al. |
| 6,485,517 B1 | | 11/2002 | Michelson |
| 6,613,091 B1 | * | 9/2003 | Zdeblick ............ A61B 17/1671 623/17.11 |
| 6,645,213 B2 | | 11/2003 | Sand et al. |
| 6,676,664 B1 | | 1/2004 | Al-Assir |
| 6,726,722 B2 | | 4/2004 | Walkenhorst et al. |
| 6,733,535 B2 | | 5/2004 | Michelson |
| 6,923,810 B1 | | 8/2005 | Michelson |
| 6,953,477 B2 | | 10/2005 | Berry |
| 7,004,945 B2 | | 2/2006 | Boyd et al. |
| 7,128,760 B2 | | 10/2006 | Michelson |
| 7,156,877 B2 | | 1/2007 | Lotz et al. |
| 7,316,689 B2 | | 1/2008 | Lieberman |
| 7,361,193 B2 | | 4/2008 | Frey et al. |
| 7,500,991 B2 | | 3/2009 | Banish, Jr. et al. |
| 7,534,265 B1 | * | 5/2009 | Boyd .................. A61F 2/28 623/17.11 |
| 7,591,852 B2 | | 9/2009 | Prosser |
| 7,637,954 B2 | | 12/2009 | Michelson |
| 7,655,010 B2 | | 2/2010 | Serhan et al. |
| 7,655,027 B2 | | 2/2010 | Michelson |
| 7,703,727 B2 | | 4/2010 | Selness |
| 7,731,751 B2 | | 6/2010 | Butler et al. |
| 7,799,081 B2 | | 9/2010 | McKinley |
| 7,837,734 B2 | | 11/2010 | Zucherman et al. |
| 7,837,735 B2 | * | 11/2010 | Malone .............. A61B 17/7064 623/17.16 |
| 7,850,733 B2 | | 12/2010 | Baynham et al. |
| 8,002,833 B2 | | 8/2011 | Monterumici et al. |
| 8,105,382 B2 | | 1/2012 | Olmos et al. |
| 8,262,666 B2 | | 9/2012 | Baynham et al. |
| 8,267,939 B2 | | 9/2012 | Cipoletti et al. |
| 8,343,193 B2 | | 1/2013 | Johnson et al. |
| 8,366,777 B2 | | 2/2013 | Matthis et al. |
| 8,992,618 B2 | | 3/2015 | Lechmann et al. |
| 9,408,719 B2 | | 8/2016 | Lechmann et al. |
| 9,700,432 B2 | | 7/2017 | Lechmann et al. |
| 10,085,851 B2 | | 10/2018 | Lechmann et al. |
| 2001/0005796 A1 | | 6/2001 | Zdeblick et al. |
| 2001/0032018 A1 | | 10/2001 | Castro et al. |
| 2002/0029082 A1 | | 3/2002 | Muhanna |
| 2002/0058947 A1 | | 5/2002 | Hochschuler et al. |
| 2002/0082700 A1 | | 6/2002 | Bianchi et al. |
| 2002/0092871 A1 | | 7/2002 | Rickard et al. |
| 2002/0147497 A1 | | 10/2002 | Belef et al. |
| 2002/0177897 A1 | * | 11/2002 | Michelson ............ A61F 2/4611 623/17.11 |
| 2003/0036762 A1 | | 2/2003 | Kerr et al. |
| 2003/0100950 A1 | | 5/2003 | Moret |
| 2004/0010260 A1 | | 1/2004 | Scribner et al. |
| 2004/0030389 A1 | | 2/2004 | Ferree |
| 2004/0068268 A1 | | 4/2004 | Boyd et al. |
| 2004/0127993 A1 | | 7/2004 | Kast et al. |
| 2004/0186572 A1 | | 9/2004 | Lange et al. |
| 2005/0038513 A1 | | 2/2005 | Michelson |
| 2005/0070900 A1 | | 3/2005 | Serhan et al. |
| 2005/0119747 A1 | | 6/2005 | Monterumici et al. |
| 2005/0149192 A1 | | 7/2005 | Zucherman et al. |
| 2005/0165483 A1 | | 7/2005 | Ray et al. |
| 2005/0261781 A1 | | 11/2005 | Sennett et al. |
| 2006/0058878 A1 | | 3/2006 | Michelson |
| 2006/0122701 A1 | | 6/2006 | Kiester |
| 2007/0161962 A1 | | 7/2007 | Edie et al. |
| 2008/0071284 A1 | | 3/2008 | Lechmann et al. |
| 2008/0133015 A1 | | 6/2008 | Lechmann et al. |
| 2015/0173913 A1 | | 6/2015 | Lechmann et al. |
| 2015/0223943 A1 | | 8/2015 | Lechmann et al. |
| 2017/0281362 A1 | | 10/2017 | Lechmann et al. |
| 2018/0055653 A1 | | 3/2018 | Lechmann et al. |

FOREIGN PATENT DOCUMENTS

| | | |
|---|---|---|
| FR | 2 836 373 A1 | 8/2003 |
| WO | 97/23174 A1 | 7/1997 |
| WO | 97/37619 A1 | 10/1997 |
| WO | 00/66044 A1 | 11/2000 |
| WO | 00/74605 A1 | 12/2000 |
| WO | 01/56513 A1 | 8/2001 |
| WO | 02/078514 A2 | 10/2002 |
| WO | 03/071992 A2 | 9/2003 |

OTHER PUBLICATIONS

U.S. Appl. No. 14/638,196, filed Mar. 4, 2015, Intervertebral Prosthesis or Disk Prosthesis.
U.S. Appl. No. 14/692,878, filed Apr. 22, 2015, Intervertebral Prosthesis or Disk Prosthesis.
U.S. Appl. No. 15/623,707, filed Jun. 15, 2017, Intervertebral Prosthesis or Disk Prosthesis.
U.S. Appl. No. 15/805,224, filed Nov. 7, 2017, Intervertebral Prosthesis or Disk Prosthesis.
European Office Action for Application No. 04729392.3, dated Mar. 28, 2017 (7 pages).
European Office Action for Application No. 04729392.3, dated Mar. 13, 2018 (6 pages).
International Search Report for Application No. PCT/CH2004/000250 dated Dec. 28, 2004 (6 pages).
International Preliminary Report on Patentability for Application No. PCT/CH2004/000250 dated Jun. 29, 2006 (14 pages).
U.S. Appl. No. 11/587,722—Non Final Office Action dated Jun. 23, 2009.
U.S. Appl. No. No. 11/587,722—Amendment in Response to Non Final Office Action.
U.S. Appl. No. 11/587,722—Final Office Action dated Jan. 25, 2010.

\* cited by examiner $$S_R = F_1 + F_2 + F_3$$

$$S_L = F_4 + F_5$$

INTERVERTEBRAL PROSTHESIS OR DISK PROSTHESIS

CROSS-REFERENCE TO RELATED APPLICATIONS

This application is a continuation of U.S. patent application Ser. No. 15/623,707, filed on Jun. 15, 2017, and entitled "Intervertebral Prosthesis or Disk Prosthesis." U.S. patent application Ser. No. 15/623,707 is a continuation of U.S. patent application Ser. No. 14/638,196, filed on Mar. 4, 2015, entitled "Intervertebral Prosthesis or Disk Prosthesis," and now issued as U.S. Pat. No. 9,700,432. U.S. patent application Ser. No. 14/638,196 is a continuation of U.S. patent application Ser. No. 11/587,723, filed on Sep. 4, 2007, entitled "Intervertebral Prosthesis or Disk Prosthesis," and now issued as U.S. Pat. No. 8,992,618. U.S. patent application Ser. No. 11/587,723 is a national stage entry pursuant to 35 U.S.C. § 371 of International Application No. PCT/CH04/00250, filed Apr. 26, 2004. Each of these applications is hereby incorporated by reference in its entirety.

FIELD

The invention relates to an intervertebral prosthesis or disk prosthesis, especially for arthrodesis surgery by means of dorsal access PLIF (posterior lumbar interbody fusion), TLIF (transforaminal lumbar interbody fusion), ELIF (extraforaminal lumbar interbody fusion), ALIF (anterior lumbar interbody fusion) and ACIF (anterior cervical interbody fusion. The objective of this surgical technique is the treatment of a degenerated or otherwise diseased intervertebral disk. The surgeon looks for access to the intervertebral disk through a centrally placed skin incision. Subsequently, he exposes the rear region of the movement segments, especially the laminae and the pedicle entry points. By means of a partial resection of the facettal and laminar components, the surgeon aims past the nerve roots and the medullary space in the direction of the diseased intervertebral disk.

BACKGROUND

For this surgical technique, only a limited amount of autologous spongiosa is available for filling the cavities of cage-like intervertebral or disk prosthesis and the spaces between individual implants and their surroundings. In the long term, the arthrodesis takes place not with the implant but between the bone and the bone replacement material. The individual implants therefore function only as place holders or spacers.

The intervertebral spaces, supplied with the known intervertebral implants, therefore frequently do not attain complete arthrodesis, that is, they end in a pseudoarthrosis. The situation is much the same also with cage-like intervertebral implants for the cervical spine, as well as for those, which were inserted through ventral entrances. Such intervertebral spaces are not stable mechanically, as would have been expected from a stiffening. The consequences then may be recurring pain with subsequent revision surgery.

For the implants and surgical techniques described above, the surgeon uses autologous bone material, which he obtains from the resected parts of the vertebral body or by means of an additional intervention in the crest of the ilium. Since dorsal accesses to the intervertebral disk space are very narrow, the applying of bone material is made difficult. The surgeon is unable to ensure that the whole of the intervertebral space is filled with autologous bone material. There is therefore the danger that empty spaces will result which, on the one hand, permits migration of the implant. On the other hand, the spaces, not filled with autologous bone material, are filled by a soft, fibrous tissue.

SUMMARY

It is an object of the invention to provide an intervertebral prosthesis or a disk prosthesis, which makes an asymmetric emergence of the osteocementum possible, so that individual regions between the vertebral bodies (for example the central and posteriors zones) are automatically supplied with more osteocementum than other regions.

This objective is accomplished by an intervertebral prosthesis or disc prosthesis, for which the outlet openings are dimensioned differently in size. The amount of osteocementum $K_L$, emerging through $S_L$ is either larger or smaller than the amount of osteocementum $K_R$ emerging through $S_R$; or the amount of osteocementum $K_H$, emerging through $S_H$, is larger or smaller than the amount of osteocementum $K_V$ emerging through $S_V$.

In other words, the outlet openings are dimensioned so that, when flowable osteocementum is supplied through the inlet opening into the cavity, the amount of osteocementum $K_L$ emerging through $S_L$ is either larger or smaller than the amount of osteocementum $K_R$ emerging through $S_R$ or the amount of osteocementum $K_H$, emerging through $S_H$, is larger or smaller than the amount of osteocementum $K_V$, emerging through $S_V$.

The invention permits the intervertebral space to be filled with synthetic bone material (osteocementum) after the cage-like intervertebral prosthesis or disk prosthesis has been placed. The implant is secured by the emergence and subsequent curing of the flowable, hydraulic osteocementum. Due to the asymmetric arrangement of the outlet openings in the implant, the osteocementum can be spread selectively. The inventive prosthesis furthermore has the advantage that it makes superfluous the additional removal of bone at the crest of the iliac, which can cause long enduring pain.

In a special embodiment, the inlet opening is provided in the front side of the prosthesis and the cavity extends from the inlet opening in the direction of the rear side.

In the case of a further embodiment, the inlet opening is disposed in the left all right side of the prosthesis and the cavity extends from the inlet opening in the direction of the opposite right or left side.

In the case of a further embodiment, the cross section of the cavity decreases at least on a partial section as the distance from the inlet opening increases. Due to the tapering of the cavity, the liquid cement mixture flows more easily through the side openings of the implant. The wall of the implant in the opening opposite the injection point has a shearing-off edge, so that the liquid cement mixture is diverted.

In the case of a further embodiment, the cavity tapers, at least on a partial section, either in wedge-shaped or conical fashion. In the case of a further embodiment, the upper and lower sides converge in the direction of the front side at least on a partial section. In yet another embodiment, the prosthesis is filled at least partially with a cured hydraulic osteocementum, which extends at least partially beyond the outlet opening.

In the case of a further embodiment, the implant may consist of two intervertebral prostheses, which are disposed next to one another, the right side of the intervertebral prosthesis disposed on the left being oriented in the direction of the left side of the intervertebral prosthesis disposed on the right. For the intervertebral prosthesis disposed on the left, the condition $S_L>S_R$ applies and for the intervertebral prosthesis on the right, the condition $S_R>S_L$.

Moreover, the intervertebral prosthesis may be varied in many ways, for example, by using flat, concave, convex or also spherical side walls.

Calcium phosphate cements, which, after the two components are mixed, may be injected in liquid form into the implant and are subsequently cured hydraulically, are suitable as flowable hydraulic osteocementum.

BRIEF DESCRIPTION OF THE DRAWINGS

The invention and further development of the invention are described in even greater detail by means of several examples and partially diagrammatic drawings, in which.

DETAILED DESCRIPTION OF THE PREFERRED EMBODIMENTS

Figure 1:
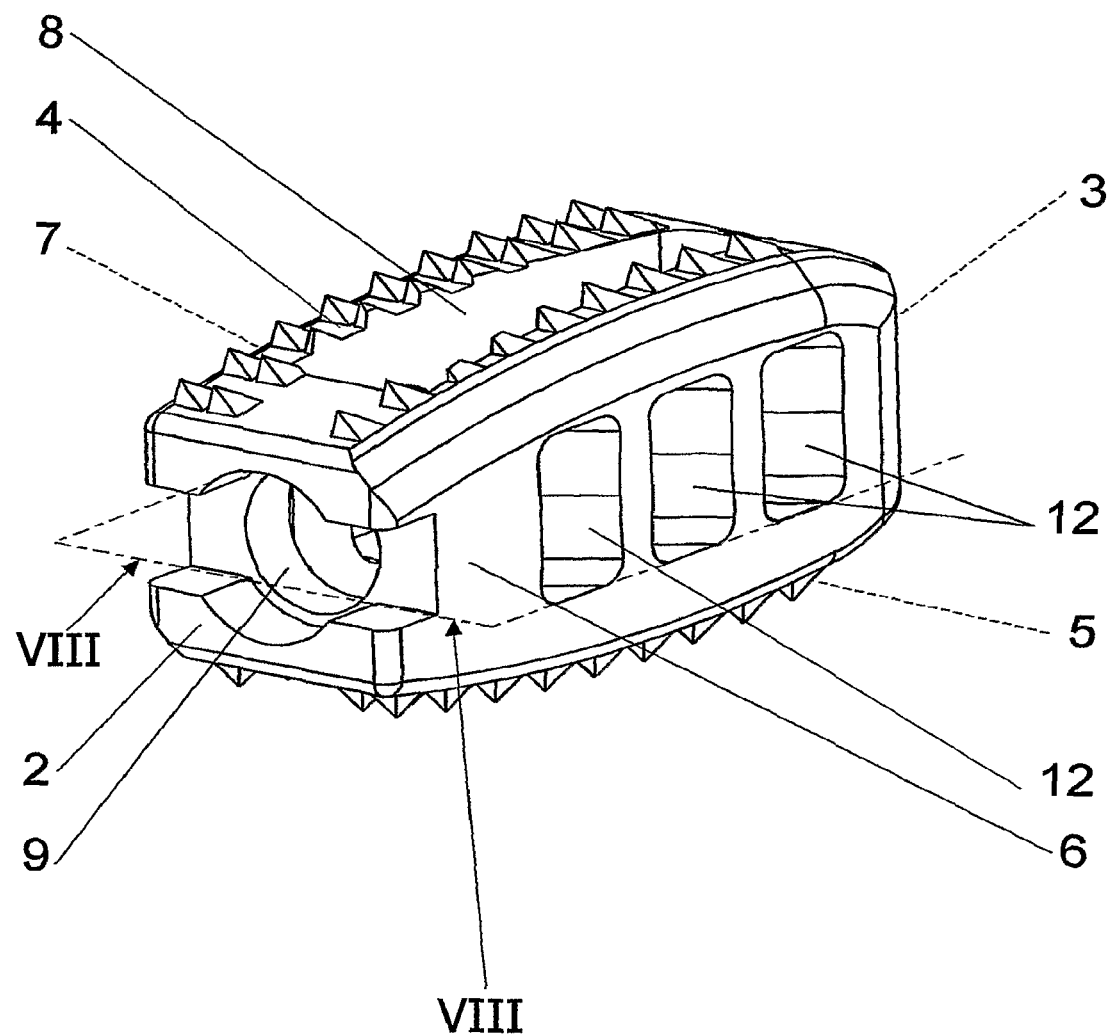
FIG. 1 shows a perspective view of an inventive, lens-shaped intervertebral implant.
Figure 2:
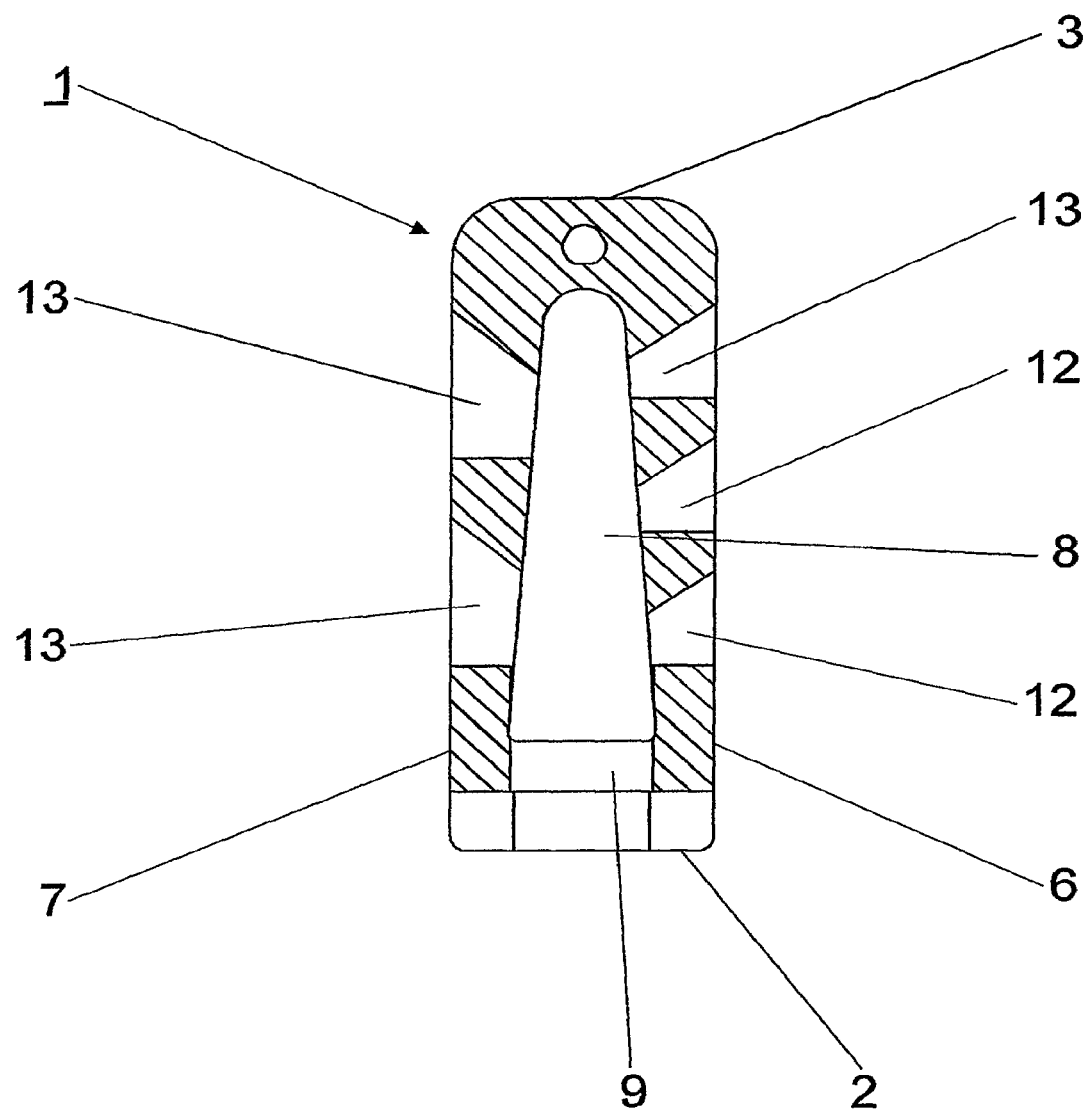
FIG. 2 shows a longitudinal section through the intervertebral implant of FIG. 1 along the central plane VIII-VIII.

The intervertebral prosthesis 1, shown in FIGS. 1 and 2, consists of a rectangular hollow body and has a front side 2, a rear side 3, an upper side 4 suitable for positioning against the baseplate of a vertebral body, a lower side 5 suitable for positioning against the baseplate of a vertebral body, a right side 6, a left side 7, a cavity 8 suitable for accommodating a flowable, hydraulic osteocementum, an inlet opening 9 into the cavity 8 and several outlet openings 10; 11; 12; 13 from the cavity 8. The upper side 4 and the lower side 5 converge toward the front side 2 as well as toward the rear side 3, so that a lens-like configuration of the intervertebral prosthesis results.

As can be seen from FIG. 2, the cross section of the cavity 8 decreases in the shape of a cone as the distance from the inlet opening 9 increases.

Figure 3:
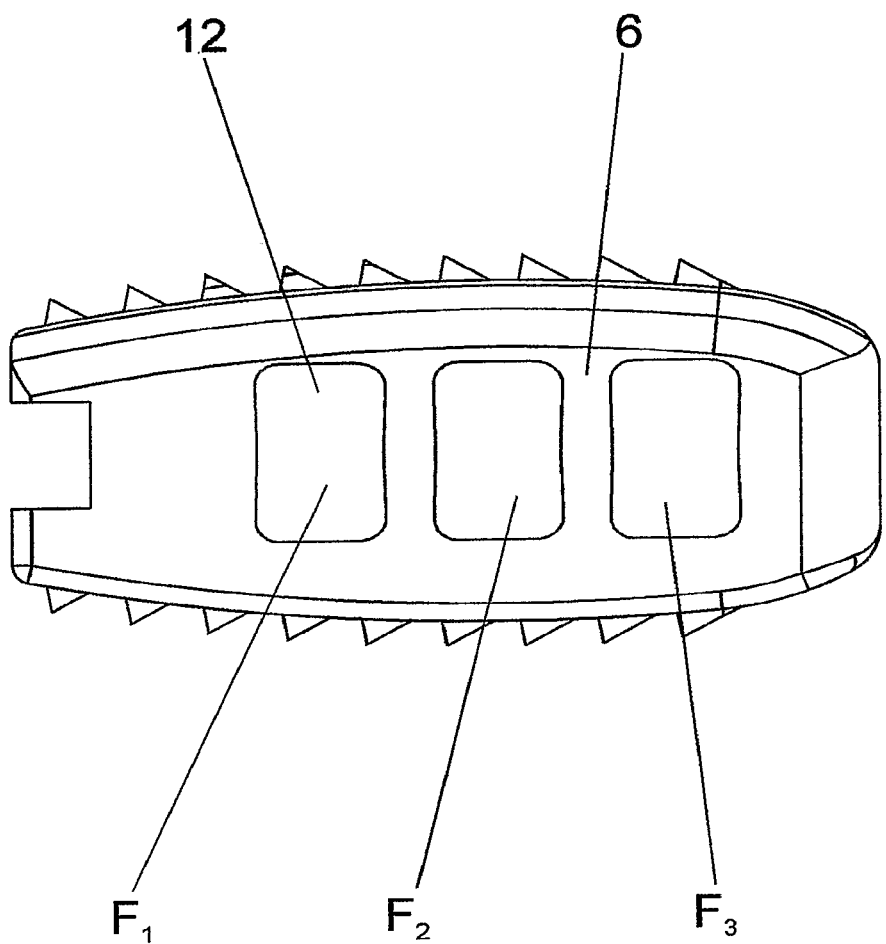
FIG. 3 shows a side view from the right of the intervertebral implant of FIG. 1.

As shown in FIG. 3, there are three outlet openings 12 with areas $F_1$, $F_2$ and $F_3$ in the right side 6 of the intervertebral prosthesis 1, so that the sum $S_R$ of the cross sectional surfaces of the outlet openings emerging the right side 6 is $S_R=F_1+F_2+F_3$.

Figure 4:
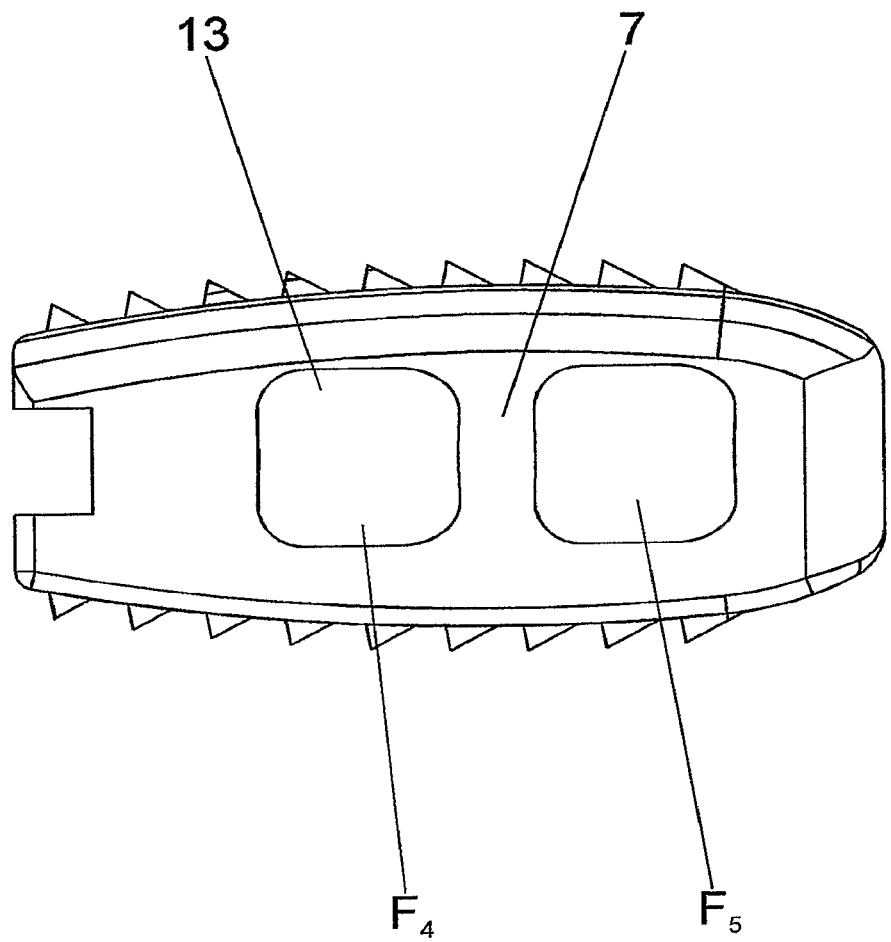
FIG. 4 shows a side view from the left of the intervertebral implant of FIG. 1.

As shown in FIG. 4, there are two outlet openings 13 with the areas $F_4$ and $F_5$ in the left side 7 of the intervertebral prosthesis 1, so that the sum $S_L$ of the cross-sectional surfaces of the outlet openings emerging for the left side 7 is $S_L=F_4+F_5$.

It is important that the sum $S_L>S_R$, so that more osteocementum can emerge on the left side 7 of the intervertebral prosthesis 1 from the cavity 8 through the outlet opening 13 into the intervertebral space than from the right side 6.

Figure 5:
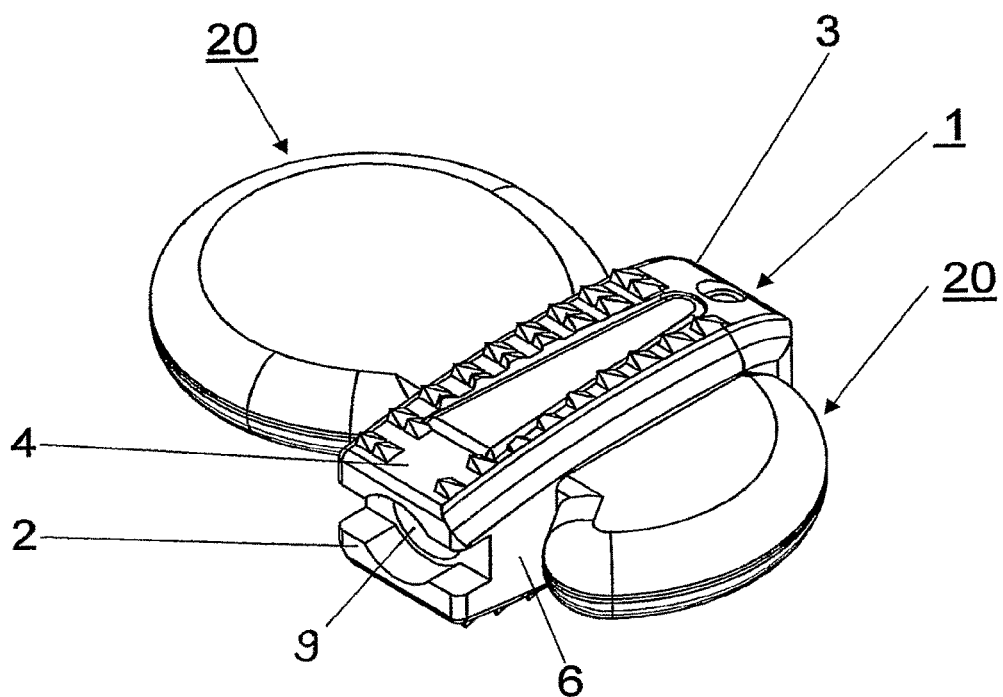
FIG. 5 shows a perspective view of an inventive intervertebral prosthesis, which is secured by means of cured osteocementum.
Figure 6:
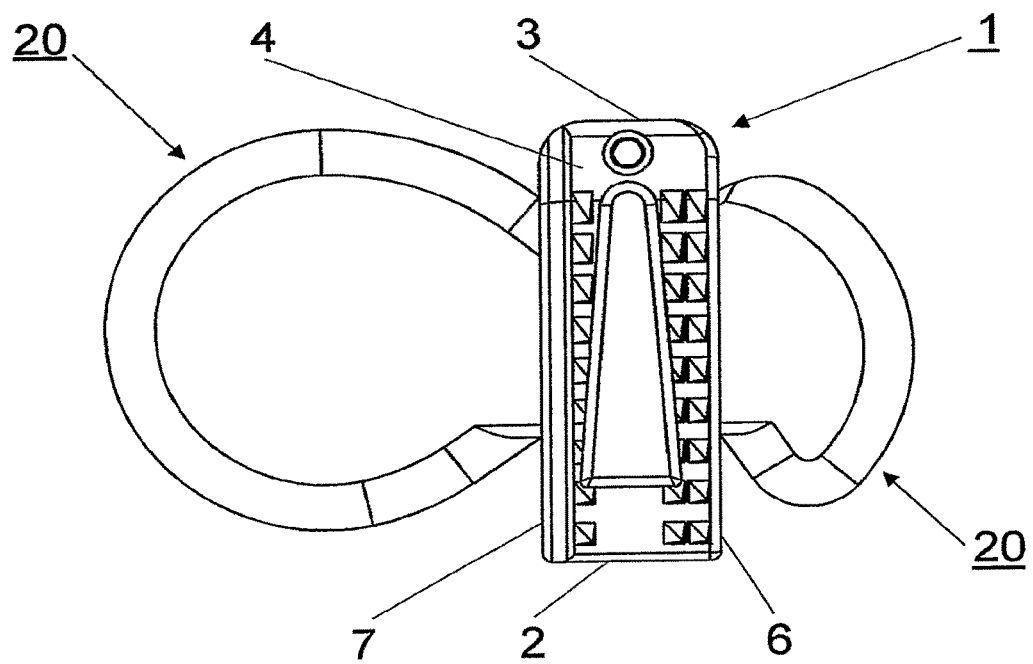
FIG. 6 shows a plan view of the intervertebral prosthesis of FIG. 5.

FIGS. 5 and 6 show how the osteocementum 20, emerging from the right side 6 and the left side 7 of the intervertebral prosthesis 1, is distributed. Because the sum $S_L$ of the cross sectional areas of the outlet openings 13 emerging on the left side 7 is larger, the amount of osteocementum 20, emerging on the left side 7 and curing, is also larger than that emerging on the right side 6 and curing.

Figure 7:
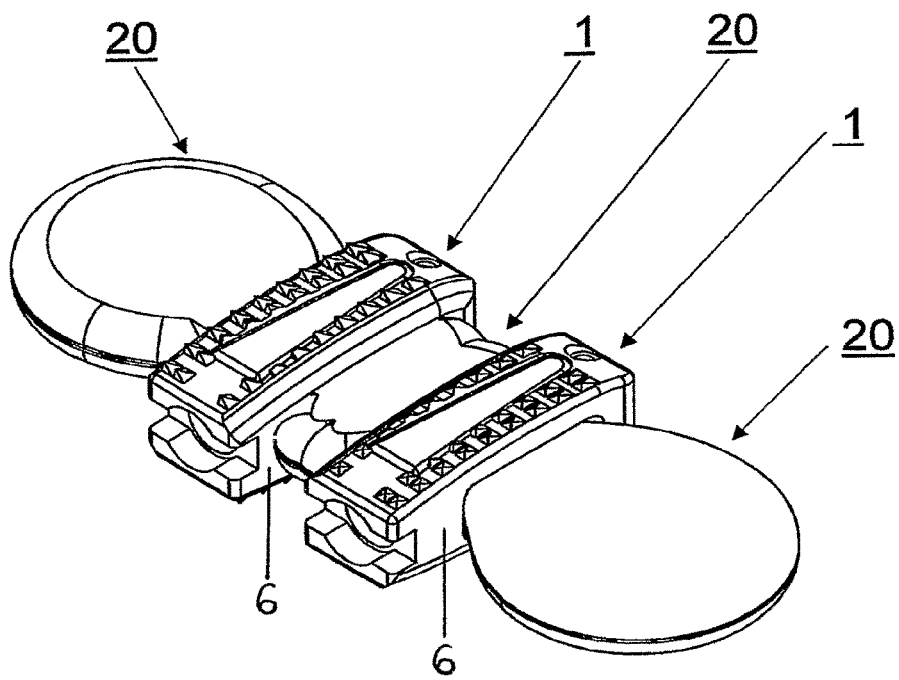
FIG. 7 shows a perspective view of a variation of the embodiment, using two intervertebral implants, the osteocementum securing the implant in their position relative to one another as well as to prevent migrating apart.
Figure 8:
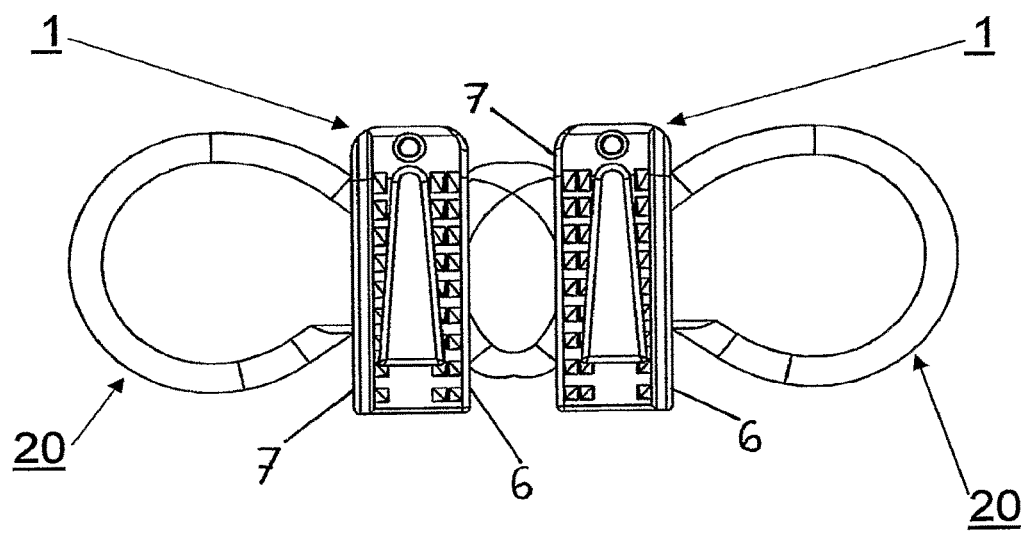
FIG. 8 shows a plan view of the two intervertebral implants of FIG. 7.

FIGS. 7 and 8 show a further embodiment, which consists of two inventive intervertebral prosthesis 1, which are disposed next to one another. The two intervertebral prostheses are positioned in such a manner, that the right side 6 of the intervertebral prosthesis 1, which is disposed on the left, is oriented in the direction of the left side 7 of the intervertebral prosthesis 1, which is disposed on the right. For the intervertebral prosthesis 1, disposed on the left, the condition $S_L>S_R$ applies, whereas, for the intervertebral prosthesis 1, which is disposed on the right, the reverse applies, namely $S_R>S_L$. Due to this measure, less osteocementum 20 emerges in the space between the two intervertebral prostheses 1 than emerges to the right side of the intervertebral prosthesis 1 disposed on the right and to the left side 7 of the intervertebral prosthesis 1 disposed on the left.

Figure 9:
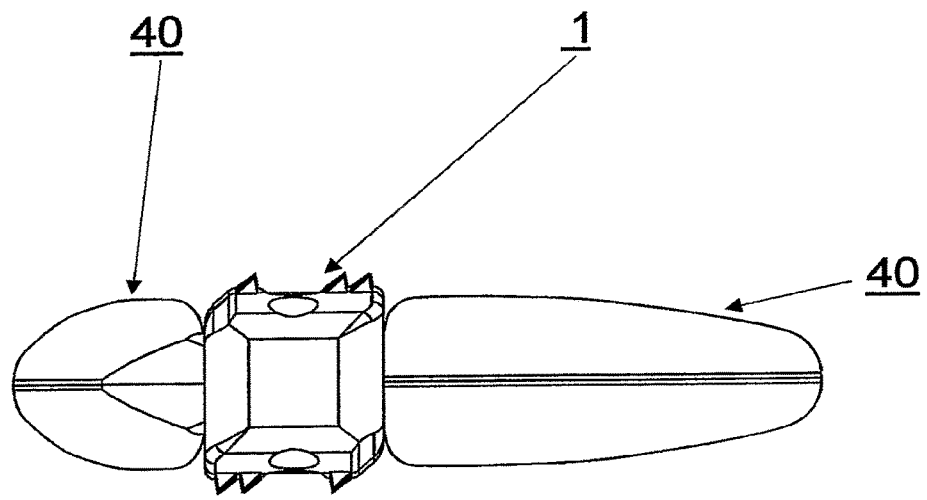
FIG. 9 shows a front view of a variation of the embodiments, in which the perforated intervertebral implant has a rectangular cross section

FIG. 9 shows a variation of the embodiment of an inventive intervertebral implant 1, which has a rectangular cross section and from which a larger amount of osteocementum 40 has emerged on the right side than on the left side.

Figure 10:
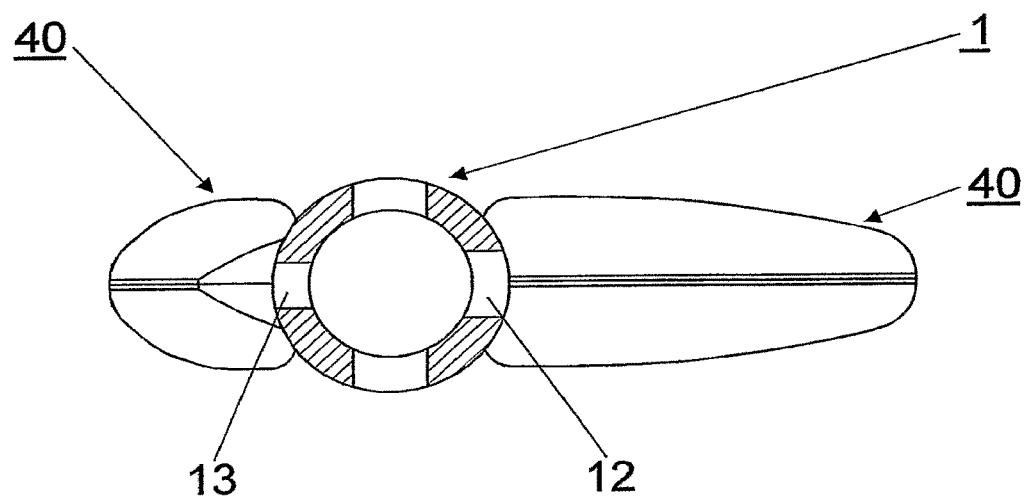
FIG. 10 shows a front view of a variation of the embodiment, in which the perforated intervertebral implant has a circular ring-shaped cross section.

FIG. 10 shows a further variation of an embodiment of an intervertebral prosthesis 1, which has a circular cross section and for which the amount of osteocementum 40 emerging on the right side through the outlet openings 12 is larger than that emerging on the left side through outlet openings 13.

The invention claimed is:

1. An intervertebral implant system for implantation between an upper vertebra and a lower vertebra, comprising:
   a first spacer, comprising:
      a cavity defined by a body having a first end and an inlet opening for receiving a flowable material to the cavity;
      a second end opposite the first end;
      an upper side for contacting at least a portion of the upper vertebra;
      a lower side for contacting at least a portion of the lower vertebra;
      a first lateral side extending between the upper and lower sides and between the first and second ends; and
      a second lateral side extending between the upper and lower sides and between the first and second ends, the second lateral side defining an opening to the cavity;
   a second spacer, comprising:
      a body having a first end and a second end opposite the first end;
      an upper side for contacting at least a portion of the upper vertebra;

a lower side for contacting at least a portion of the lower vertebra;

a first lateral side extending between the upper and lower sides and between the first and second ends; and a second lateral side extending between the upper and lower sides and between the first and second ends;

wherein the first and second spacers are sized and configured to be positioned in an intervertebral space a distance apart from one another with the second lateral side of the first spacer facing the first lateral side of the second spacer, such that a volume of flowable material delivered to the inlet of the first spacer flows through the cavity of the first spacer, out at least one of the first and second lateral sides, into a central region of the disc space disposed between the first and second spacers, and to the first lateral side of the second spacer, wherein the first spacer is configured to have the flowable material emerge asymmetrically from the first spacer such that more of the flowable material emerges from one of the first and second lateral sides of the first spacer than from an opposite one of the first and second lateral sides of the first spacer, and wherein at least one of the first and second lateral sides of the first spacer are substantially straight.

2. The intervertebral implant system of claim 1, wherein the first end of the first spacer is configured to engage a delivery tool.

3. The intervertebral implant system of claim 1, wherein the first lateral sides of each of the first and second spacers are substantially straight and each have a first length extending between the respective first and second ends and a first height extending between the respective top and bottom surfaces.

4. The intervertebral implant system of claim 3, wherein the second lateral sides of each of the first and second spacers are substantially straight and each have a second length extending between the respective first and second ends and a second height extending between the respective top and bottom surfaces, wherein the first length is substantially the same as the second length and the first height is substantially the same as the second height.

5. The intervertebral implant system of claim 1, wherein the top surface and the bottom surface converge towards the second end at least on a partial section.

6. The intervertebral implant system of claim 1, wherein the cavity comprises a cross-sectional area and the cavity extends from the inlet opening towards the second end.

7. The intervertebral implant system of claim 1, comprising an insertion tool for conveying the flowable medium to the first spacer.

8. The intervertebral implant system of claim 1, wherein at least one of the first and second spacers has a rectangular cross section.

9. The intervertebral implant system of claim 1, wherein a cross-sectional area of the cavity decreases as a distance from the inlet opening increases.

10. The intervertebral implant system of claim 1, wherein the cavity extends from the inlet opening towards the second end.

11. The intervertebral implant system of claim 1, wherein a cross-sectional area of the cavity decreases in one of a wedge-shape or a conical shape.

12. The intervertebral implant system of claim 1, comprising a delivery tool configured to deliver the flowable material to the cavity.

13. The intervertebral implant system of claim 1, therein the flowable material comprises osteocementum.

* * * * *